United States Patent [19]
Glotz

[11] Patent Number: 5,736,136
[45] Date of Patent: Apr. 7, 1998

[54] IMMUNOGLOBULIN INFUSION IN XENOTRANSPLANTATION

[75] Inventor: Denis Glotz, Paris, France

[73] Assignee: SangStat Medical Corporation, Menlo Park, Calif.

[21] Appl. No.: 585,606

[22] Filed: Jan. 16, 1996

Related U.S. Application Data

[63] Continuation of Ser. No. 75,127, Jun. 11, 1993, abandoned.

[51] Int. Cl.$^6$ .......................... C07K 16/00; A61K 31/00; A61K 39/395
[52] U.S. Cl. ...................... 424/132.1; 514/21; 530/387.1
[58] Field of Search ...................... 530/387.1; 424/85.8, 424/132.1; 514/21

[56] References Cited

PUBLICATIONS

Glotz, D. et al., "Inhibition of Anti–HLA Antibodies AB Cytotoxicity and Synthesis by Intravenous Polyclonal Immunoglobulins IVIG", 25th Annual Meeting of the American Society of Nephrology, Baltimore, Maryland, USA, Nov. 15–18, 1992. J Am Soc Nephrol 3(3). 1992 860, XP002041267.
Magee et al. Therapeutic Immunology 1:45–58, 1994.
Platt et al., Connecticut Medicine 8:468–70, 1991.
Basta et al., The J. Clin Invest. 84:1974–81, 1989.
Bach et al, Transplantation Proc. 24:49–52, 1992.
Dalmasso et al. Clin Eup. Immunol. 86:31–35 1991.
Sullivan et al, New Engl J. Med. 323:705–712, 1990.
Platt et al., Immunology Today 11:450–456, 1990.
Somerville et al. Kidney Int'l. 44 Suppl. 42:5112–5121, Jun. 16, 1993.
Kahan et al. Immunological Reviews 136:29–49, 1993.
Kupin et al. Transplantation 40:601–604, 1985.
Cottler–Fox et al. Experimental Hematology 16:518, 1988.
Gale et al. Cancer 68(6 suppl.):1451–1453, 1991.
Schulak et al. J. Surg. Res. 25:562–571, 1978.
Auchincloss, Transplantation 46:1–20, 1988.
Sharabi et al. J. Exp. Med. 172:195–202, 1990.
Blanchette et al., "Role of Intravenous Immunoglobulin G in Autoimmune Hematologic Disorders", *Seminars in Hematology*, 29(No 3, Suppl 2):72–82 (1992).
Budde et al., "Reticuloendothelial System Fc–receptor Function in Patients with Immune Thrombocytopenia After Treatment with High Dose Intravenous Immunoglobulin", *Scand. J. Haematol.*, 37:125–129 (1986).
Bussel, "The Use of Intravenous γ–Globulin in Idiopathic Thrombocytopenic Purpura", *Clinical Immunology and Immunopathology*, 53:S147–S155 (1989).
Dodd, "Hepatitis C Virus, Antibodies, and Infectivity; Paradox, Pragmatism and Policy", *Am. J. of Clinical Pathology*, 97(1):4–6 (1992).
Mitra et al., "Elimination of Infectious Retroviruses During Preparation of Immunoglobulins", *Transfusion*, 26(4):394–397 (1986).
Siber et al., "Preparation of human Hyperimmune Globulin to *Haemophilus Influenzae* b, *Streptococcus Pneumoniae*, and *Neisseria Meningitidis*", *Infection and Immunity*, 45(1):248–254 (1984).

*Primary Examiner*—Lila Feisee
*Assistant Examiner*—Geetha P. Bansal
*Attorney, Agent, or Firm*—Flehr Hohbach Test Albritton & Herbert LLP; Richard F. Trecartin

[57] ABSTRACT

Intravascular introduction of pooled immunoglobulin is employed prior to xenotransplantation to extend the effective lifetime of the donor organ. In particular, intravenous administration of concentrated immunoglobulin for intravenous use (IVIg) by itself, or in combination with immunosuppressive agents is used to enhance the survival time of xenografts.

9 Claims, No Drawings

IMMUNOGLOBULIN INFUSION IN XENOTRANSPLANTATION

This application is a continuation of 08/075,127 filed Jun. 11, 1993, (now abandoned).

TECHNICAL FIELD

The field of this invention is the use of intravenous immunoglobulin in xenograft transplantation.

BACKGROUND

Transplantation of bone marrow and organs has become a major therapy for a large number of diseases. By using organs which are to varying degrees matched to the recipient, the organ can have effective long-term function. In many cases, donors are not available to provide organs which are reasonably matched to the recipient and the recipient is forced to wait extended periods of time until a donor can be found. However, the diseased organ may cease to function and frequently mechanical alternatives to the diseased organ are neither satisfactory nor available. In these situations, there has been some consideration given to using xenotransplantation. Thus, one could use an organ from a species which is relatively close in the evolutionary pathway to humans, or even with other species as appropriate, while the patient awaits an appropriate allogeneic organ. In this manner, the patient may be at least maintained for reasonable periods of time with a functioning organ, while a more suitable long-term replacement organ is sought.

As already indicated, there are problems using organs which are not HLA matched, where the recipient's immune system rejects the transplanted organs. The situation is particularly exacerbated when a xenogeneic organ is involved. Severe immunosuppression, using immunosuppressants, such as Cyclosporine A, have not proven adequate. There is, therefore, substantial interest in being able to find alternative approaches to extending the useful lifetime of xenotransplants.

Relevant Literature

Blanchette et al., (1992) Semin. Hematol. 29 (3 Suppl 2) 72–82 reviews the role of intravenous immunoglobulin ("IVIg") in autoimmune hematologic disorders. See also, Bussel (1989) Clin. Immun. Immunopathol. 53, pS 147–155). Budde et al, (1986) Scand. J. Haematol. 37, 125–129 describes the Fc-receptor function after treatment of patients with IVIg. Cohn fractionalions are described in Dodd et al. (1992) Am J Clin Path 97, 4–6; Mitra et al (1986) Transfusion 26, 394–397; and, Siber et al. (1984) Infect Immun 45, 248–254.

SUMMARY OF THE INVENTION

Administration of concentrated immunoglobulin fraction into the vascular system of a mammalian host is performed prior to and optionally subsequent to xenotransplantation. Particularly, the fraction is a concentrated composition of immunoglobulins from a plurality of donors which is injected intravenously into the host, by itself or in conjunction with other agents. According to a preferred embodiment, human IgG fraction is commercially available IVIg (Pasteur-Merieux, Lyon, France) obtained from human blood using the Cohn cold ethanol fractionation method. Administration of the fraction provides for immunosuppression of the host and delays the onset of or reduces the likelihood or intensity of graft rejection.

DESCRIPTION OF THE SPECIFIC EMBODIMENTS

Methods are provided for the treatment of patients receiving transplantations, particularly xenotransplantations. The methods comprise intravenous administration of concentrated immunoglobulin compositions.

For the most part, humans will be the host/recipient, but in some situations, the subject methodology may find application with rare or highly valuable domestic animal hosts. The xenotransplant generally derives from a species related to that of the graft recipient; meaning they are generally of the same class, preferably of the same order, more preferably of the same family, e.g., rodent to rodent, ovine to ovine, equine to equine, canine to canine and primate to primate. For humans, the xenotransplant will usually derive from a primate, e.g. baboon, though other mammals, such as pig may be used.

The immunoglobulin compositions are obtained by fractionating blood, preferably human blood. In a particular embodiment, the compositions are derived from human placental blood. A concentrated immunoglobulin fraction may be prepared by chromatography (affinity, ionic exchange, gel filtration, etc.), selective precipitation with salts such as ammonium sulfate, organic solvents such as ethanol, or polymers such as polyethyleneglycol, though cold-ethanol fractionation (using the Cohn method fractions II and III) is preferred.

The fractionated antibodies may be dissolved or diluted in any non-toxic, non-pyrogenic media suitable for intravenous administration in human, for instance, sterile buffered saline. Such immunoglobulin preparations, suitable for human intravenous administrations are refered to as IVIg. The IVIg solutions used for administration are generally characterized by having an average population of antibodies, without any particular specificity; having from 2 to 200 mg/ml more usually from about 10 to 100 mg/ml protein; and being preferably primarily of the IgG isotype, although isotypic mixtures including IgA and IgM isotypes also may be used. Generally the IVIg is obtained commercially from available mixed normal human immunoglobulin preparations for intravenous use, a preferred source being the IVIg fraction commercially available from Pasteur-Merieux (Lyon, France). Such commercial IVIg compositions may be obtained dry or in solution.

Prior to administration, the immunoglobulin fraction may be subject to treatment such as enzymatic digestion (e.g. with pepsin, papain, plasmin, glycosidases, nucleases, etc.), heating, etc. and/or further fractionated but will normally be used as commercially available. Thus, administered compositions may comprise primarily intact antibody, antibody fragments, or mixtures thereof. Where the compositions comprise primarily antibody fragments, Fc containing fragments will predominate. Hence, by IVIg fragments is meant preparations of immunoglobulin fragments, primarily Fc fragments, suitable for human intravenous administration.

The IVIg composition is administered into the vascular system, conveniently intravenously by infusion and preferably prior to the xenotransplant. As used herein, the term "infusion" is used for convenience and includes a variety of means of administering an effective dosage of IVIg to the vascular system of the host, including injection. Administration of the effective dosage may occur in a single infusion or a series of infusions. While infusions two weeks prior to transplantation are found to be effective in many cases, administraion is usually performed within about 24 hours, more usually within about 8 hours, and may be within one hour or less of the time of the transplantation. In one embodiement, a series of between 2 and about 5 infusions are made beginning between 1 and 15 days before transplantation. Graft survival may also be enchanced by post-transplantation administration of the IVIg compositions. While a single infusion within 4 min post-transplantation finds limited use, where post-transplantation infusions are used, they are preferably provided as one or more post-transplantation "booster" infusions following one or more pre-implantation administrations.

An effective dosage reduces the host immune rejection response as measured by a significant increase in xenograft survival time as compared to untreated hosts. At an effective dosage, graft survival time increases by at least about 100%, preferably at least about 300%, more preferably at least about 1,000% or more as compared with the untreated host or control protein treated host. Under optimized dosage, graft survival time can be increased over 10 fold and even 100 fold with the disclosed methods. Graft survival is generally determined by organ/tissue function, such as contraction, secretion, pharmacological responsiveness, etc., or by cellular function, such as electrical potentials, dye exclusion, or other indicia of viability. Generally, an effective dosage will total from about 0.01–10, more usually from about 0.05–5, and most usually from about 0.2–2 g IVIg protein per kg of host body weight. Where the dosage is administered in a plurality of infusions, generally at least half of the total dosage will be provided within 72 hours prior to transplantation.

The immunoglobulin composition is conveniently administered by means of a catheter implanted into an appropriate vein. The composition is administered at a moderate rate, generally ranging from about 10 min-6 h, more usually from about 30 min-3 h, in accordance with the rate at which the liquid can be accepted by the patient. Samples of blood may be taken to determine the level of immunoglobulin in the bloodstream to ensure that an effective concentration, empirically determined from the above dosage guidlines, has been achieved.

The subject methodology may be used with any type of xenotransplantation, particularly heart, kidney, lung, pancrease, liver and intestive.

The subject treatment may be employed in conjunction with conventional immunosuppressants at dosages sufficient to inhibit immune rejection. Typically, effective immunosuppressant dosages useful in the subject methods are the same or less than conventional dosages. Cyclosporine A, F-K506, immunosupressive monoclonal antibodies, etc. may find application concurrent with the administration of IVIg or subsequent to the xenotransplant.

Except for the administration of the subject compositions, the xenotransplantation is performed in substantially the same manner as any other transplantation.

The following examples are offered by way of illustration and not by way of limitation.

EXPERIMENTAL

Materials and Methods

Hartley guinea pigs and Lewis rats were obtained from CSEA la Source (Orleans, France).

The polyclonal immunoglobulins for intravenous use (IVIg), collected from a large pool of normal human donors were obtained as intact immunoglobulins (Gamma-PEG) from Pasteur-Merieux (Lyon, France).

Human albumin was obtained from the Centre National de Transfusion Sanguine, Paris, France.

Surgical Procedure:

Harvesting of the Guinea pig heart was done under general heparinization after injection of 40 ml of cardioplegic solution. After anesthesia of the recipient rat with ether, the cardiac graft was connected by the donor's aorta to the recipient's aorta and by the donor's pulmonary artery to the recipient's inferior vena cava.

IVIg Administration:

IVIg (Gamma—PEG) was given intravenously in 90 min. at a dose of 1 g/kg body weight, just prior to transplantation, through a catheter implanted in the internal jugular vein. Control rats received an equivalent dose of human albumin using the same procedure.

Evaluation:

Graft function was defined by the existence of ventricular contractions, determined every 5 min. for the first hour, then every 15 min.

The following table indicates the results, where three different groups of rats were studied.

| GROUP | PERFUSION | GRAFT SURVIVAL (minutes) |
|---|---|---|
| I | none | 4'30/6'4'30/4+30/6' |
| II | Albumin | 12'/11'30/13'7/14'30/8'30 |
| III | IVIg | 90'/120/90/20'/63' |
| | | $p < 0.005$ vs I and II |

The above results demonstrate that the infusion of the IVIg just before xenotransplantation significantly delays the hyperacute rejection. The reason the improvement is achieved is unknown, but an order of magnitude or greater may be achieved as compared to no treatment or providing albumin.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed:

1. A method for enhancing the survival of a mammalian xenotransplant in a mammalian host, said method comprising:

administering to said host a dosage of intravenous immunoglobulin (IVIg) effective to reduce or delay the immune hyperacute rejection response of said host, whereby the survival time of said xenotransplant is increased.

2. A method according to claim 1, wherein said dosage is in the range of 0.02 to 2.0 g of protein per kg of host.

3. A method according to claim 1, wherein said IVIg is obtained by Cohn cold-ethanol fractionation of human blood.

4. A method according to claim 1, wherein said dosage is provided intravenously.

5. A method according to claim 1, wherein said dosage is provided by a plurality of administrations, wherein at least one of said administrations is provided within 72 hours before xenotransplantation.

6. A method according to claim 1, wherein an immunosuppressant drug is administered after said xenotransplant in an amount sufficient to further reduce or delay immune rejection response of said host, whereby the survival time of said xenotransplant is further increased.

7. A method according to claim 1, wherein said xenotransplant is a heart, a kidney, a liver, or a lung.

8. A method according to claim 1, wherein said xenotransplant is from a related species.

9. A method for enhancing the survival of a mammalian xenotransplant in a mammalian host, wherein said xenotransplant and said host are of the same order, said method comprising:

within 12 hours prior to transplantation of said xenotransplant, administering to said host a dosage of IVIg in the range of 0.5 to 2 g of protein/kg of host intravenously, whereby the survival time of said xenotransplant during hyperacute rejection is increased at least 4 fold as compared with the survival time of said xenotransplant in an untreated host.

* * * * *